US008361500B2

(12) United States Patent
Qiu et al.

(10) Patent No.: US 8,361,500 B2
(45) Date of Patent: Jan. 29, 2013

(54) TABLET FORMULATIONS CONTAINING 8-[{1-(3,5-BIS-(TRIFLUOROMETHYL)PHENYL)-ETHOXY}-METHYL]-8-PHENYL-1,7-DIAZA-SPIRO[4.5]DECAN-2-ONE SALTS AND TABLETS MADE THEREFROM

(75) Inventors: Zhihui Qiu, Bridgewater, NJ (US); Wing-Kee Philip Cho, Princeton, NJ (US); Na Zhao, Belle Mead, NJ (US); Victor Ming-she Wong, Berkeley Heights, NJ (US)

(73) Assignee: Opko Health, Inc., Miami, FL (US)

( * ) Notice: Subject to any disclaimer, the term of this patent is extended or adjusted under 35 U.S.C. 154(b) by 489 days.

(21) Appl. No.: 12/531,966

(22) PCT Filed: Mar. 20, 2008

(86) PCT No.: PCT/US2008/003653
§ 371 (c)(1),
(2), (4) Date: Dec. 22, 2009

(87) PCT Pub. No.: WO2008/118331
PCT Pub. Date: Oct. 2, 2008

(65) Prior Publication Data
US 2010/0104637 A1      Apr. 29, 2010

Related U.S. Application Data

(60) Provisional application No. 60/919,501, filed on Mar. 22, 2007.

(51) Int. Cl.
| *A61K 9/20* | (2006.01) |
| *A61K 9/28* | (2006.01) |
| *A61K 31/44* | (2006.01) |
| *A01N 43/42* | (2006.01) |
| *C07D 491/00* | (2006.01) |
| *C07D 495/00* | (2006.01) |
| *C07D 491/10* | (2006.01) |
| *C07D 497/20* | (2006.01) |
| *C07D 215/00* | (2006.01) |
| *C07D 219/00* | (2006.01) |

(52) U.S. Cl. ........ 424/464; 424/465; 424/474; 514/278; 546/16; 546/19; 548/410

(58) Field of Classification Search ............... 424/464, 424/465, 474; 514/278; 546/16, 19; 548/410
See application file for complete search history.

(56) References Cited

U.S. PATENT DOCUMENTS

| 6,499,984 | B1 | 12/2002 | Ghebre-Sellassie et al. | |
| 7,563,801 | B2 * | 7/2009 | Qiu et al. | 514/278 |
| 7,981,905 | B2 * | 7/2011 | Qiu et al. | 514/278 |
| 8,178,550 | B2 | 5/2012 | Hu et al. | |
| 2003/0158173 | A1 | 8/2003 | Paliwal et al. | |
| 2005/0131011 | A1 | 6/2005 | Stupple | |
| 2007/0244142 | A1 | 10/2007 | Hu et al. | |
| 2012/0015921 | A1 * | 1/2012 | Qiu et al. | 514/171 |

FOREIGN PATENT DOCUMENTS

| WO | WO 96/26726 | 9/1996 |
| WO | WO 03/051840 | 6/2003 |
| WO | WO 2005/063243 | 7/2005 |
| WO | WO2005 063243 A1 * | 7/2005 |
| WO | WO 2006/065654 | 6/2006 |
| WO | WO 2007/114921 | 10/2007 |
| WO | WO 2007/117486 | 10/2007 |
| WO | WO 2008/118331 | 10/2008 |

OTHER PUBLICATIONS

International Search Report for PCT/US2007/008345 (Publication No. WO 2007/114921) mailed Jan. 22, 2008.
Written Opinion for PCT/US2007/008345 (Publication No. WO 2007/114921) mailed Jan. 22, 2008.
International Preliminary Report on Patentability for PCT/US2007/008345 (Publication No. WO 2007/114921) mailed Oct. 8, 2008.
International Search Report for PCT/US2008/003653 (Publication No. WO 2008/118331) mailed Feb. 17, 2009.
Written Opinion for PCT/US2008/003653 (Publication No. WO 2008/118331) mailed Feb. 17, 2009.
International Preliminary Report on Patentability for PCT/US2008/003653 (Publication No. WO 2008/118331) mailed Sep. 22, 2009.
International Search Report for PCT/US2007/008344 (Publication No. WO 2007/117486) mailed Oct. 25, 2007.
Written Opinion for PCT/US2007/008344 (Publication No. WO 2007/117486) mailed Oct. 25, 2007.
International Preliminary Report on Patentability for PCT/US2007/008344 (Publication No. WO 2007/117486) mailed Oct. 8, 2008.
Noory, et al., "Steps for Development of a Dissolution Test for Sparingly Water Soluble Drug Products," *Dissolution Technologies*, Feb. 2000, Article 3.
Reddy, et al., "Novel Neurokinin-1 antagonist as antiemetics for the treatment of chemotherapy-induced emesis," *Supportive Cancer Therapy*, Apr. 1, 2006: 3(3):140-2.
Miaskkowski, et al., Cancer Pain, Nov. 2005.
Database Prousddr Prouse Science; Provenza 388, Barcelona, Spain May 2004.

* cited by examiner

*Primary Examiner* — Richard Schnizer
*Assistant Examiner* — Jane C Oswecki
(74) *Attorney, Agent, or Firm* — Choate, Hall & Stewart, LLP; Brenda Herschbach Jarrell; Kristen C. Buteau

(57) ABSTRACT

Pharmaceutical formulations containing a salt of (5S,8S)-8-[{(1R)-1-(3,5-Bis-(trifluoromethyl)phenyl)-ethoxy}-methyl]-8-phenyl-1,7-diazaspiro[4.5]decan-2-one, represented by Formula I, which are suitable for forming into a tablet dosage form, as well as tablet dosage forms are disclosed. Disclosed also are methods of treatment utilizing such dosage forms.

9 Claims, No Drawings

TABLET FORMULATIONS CONTAINING 8-[{1-(3,5-BIS-(TRIFLUOROMETHYL)PHENYL)-ETHOXY}-METHYL]-8-PHENYL-1,7-DIAZA-SPIRO[4.5]DECAN-2-ONE SALTS AND TABLETS MADE THEREFROM

CROSS-REFERENCE TO RELATED APPLICATIONS

This application is commencing national stage examination pursuant to 35 U.S.C. §371 from International patent application No. PCT/US2008/003653 filed in the U.S. PCT receiving office on Mar. 20, 2008, which international application is based on and claims the priority of U.S. provisional patent application Ser. No. 60/919,501 filed Mar. 22, 2007. Each of the aforementioned PCT and Provisional applications is incorporated in its entirety by reference as if fully set forth herein.

FIELD OF THE INVENTION

This application generally relates to pharmaceutical formulations comprising a salt of 8-[{1-(3,5-Bis-(trifluoromethyl)phenyl)-ethoxy}-methyl]-8-phenyl-1,7-diazaspiro[4.5]decan-2-one useful for preparing a tablet oral dosage form and treatment methods employing the same.

BACKGROUND OF THE INVENTION

Identification of any publication, patent, or patent application in this section or any section of this application is not an admission that such publication is prior art to the present invention.

Certain diazaspirodecan-2-ones, for example, 8-[{1-(3,5-Bis-(trifluoromethyl)phenyl)-ethoxy}-methyl]-8-phenyl-1,7-diazaspiro[4.5]decan-2-one, for example, (5S,8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) are useful antagonists of neuropeptide neurokinin-1 receptors (the "NK-1" receptor antagonists) in the treatment of certain medical conditions, for example, two of the most debilitating side effects of cytotoxic chemotherapy, delayed-phase nausea and vomiting (chemically-induced nausea and emesis, CINE). In therapy utilizing cytotoxic chemotherapy, delayed-phase CINE manifests from between 2 days and 5 days post chemotherapy administration. Acute-phase CINE has been managed by administering a 5HT3 receptor antagonists (e.g., ondansetron), often in combination with a corticosteroid, for example, dexamethasone. This treatment has not been effective in managing delayed-phase CINE. It is believed that acute-phase CINE and delayed-phase CINE arise from different physiological phenomena. It is believed that administration of the NK-1 receptor antagonist of Formula I, or a salt thereof, for example, one or more salts of (5S,8S)-8-[{(1R)-1-(3,5-Bis-(trifluoromethyl)phenyl)-ethoxy}-methyl]-8-phenyl-1,7-diazaspiro-[4.5]decan-2-one, either alone or in combination with one or more of a corticosteroid, for example, dexamethasone and/or a 5HT3 receptor antagonist, for example, ondensetron, granisetron, palonosetron, dolasetron, or tropisetron will provide a therapy effective in treatment of CINE in humans.

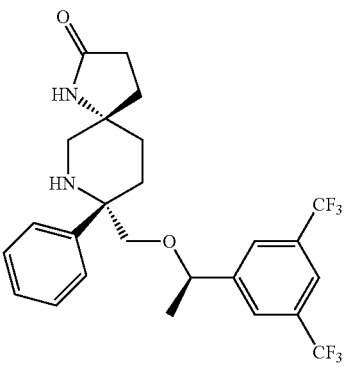

Formula I

Synthesis of the compound of Formula I is described in U.S. Pat. No. 7,049,320, issued May 23, 2006 (the '320 patent), U.S. provisional application No. 60/919,666, filed Mar. 22, 2007, and in an international application co-filed in the U.S. receiving office with the present application under Attorney's docket no. CD06628L01US on Mar. 20, 2008, each of which are incorporated herein by reference in their entirety.

Compounds having therapeutic activity must be provided to a patient in a suitable formulation to take advantage of their therapeutic properties. In general, dosage forms suitable for oral administration are preferred. Oral formulations are easy to administer using a non-invasive procedure. Oral dosage forms provide the medicament in a form that is robust in the environment in which it is handled, administered, and stored. Moreover, tablet oral dosage forms conveniently offer the medicament in a variety of discrete dosage sizes and can provide the active pharmaceutical ingredient in a minimum volume per dosage unit. In addition, a tablet can be prepared in fewer unit operations than capsule dosage forms, and tablets, through the provision of tablet "scores", offer the potential of providing user-selectable multiple dosage strengths using a single dosage unit. Such convenience is unavailable in a capsule dosage form. On the other hand, in many instances, the active pharmaceutical ingredients used in pharmaceutical formulations (API, also termed herein, "drug substance"), especially those having a crystalline form, are not by themselves suitable for forming into a tablet, especially a tablet formed using direct compression techniques. To enable formation of a tablet which can be handled and stored without breakage or loss of material from the tablet (that is, a tablet having low percentage friability), the drug substance must be combined with excipients in a formulation that enables formation of a tablet that is sufficiently robust to withstand handling and storage until the point of use. Moreover, once formed into a tablet, the tableted formulation must be capable of readily releasing the API at a desired point within the gastrointestinal tract when administered to an end user.

OBJECTIVES AND SUMMARY OF THE INVENTION

In view of the foregoing, what is desired is a compressible formulation suitable for providing a tablet dosage form containing a salt of the compound of Formula I and the tablet dosage form provided therefrom. What is desired also is a dosage form that provides therapeutically effective serum levels of the therapeutic agent and is robust toward degradation under the environmental conditions in which it is handled and stored.

The above and other objectives are provided by the present invention, which in one aspect provides a powdered pharmaceutical formulation comprising: (a) a granulate comprising at least one crystalline salt of Formula I, intragranular microcrystalline cellulose, lactose monohydrate, a first disintegrant, and a binder; and dry-blended therewith (b) extragranular microcrystalline cellulose, a second disintegrant, and magnesium stearate, wherein the amounts of the constituents and the agglomeration technique used to prepare said granulate is selected to provide a formulation that, upon compression in a tablet press, yields a pressed tablet having a hardness of at least 10 kp.

In some embodiments it is preferred for the disintegrant to be croscarmellose sodium. In some embodiments it is preferred to select the binder from providone K30, pregelatinized starch, and hypromellose 2910, 6 cps, more preferably, the binder is providone K30. In some embodiments it is preferred for the preparation of the granulate to include an agglomerating technique utilizing a granulating fluid which contains a binder, wherein the binder is selected from providone K30 and hypromellose 2910, 6 cps, more preferably the binder in the granulating fluid is providone K30. In some embodiments it is preferred to employ an agglomerating technique utilizing a granulating fluid containing a binding agent that provides a granulate having a is bulk density about 0.50 g/ml to about 0.60 g/ml and a tapped density of from about 0.65 g/ml to about 0.72 g/ml. In some embodiments it is preferred to employ a wet-granulating technique following agglomeration to provide the granulate constituent of the compressible formulation.

In some embodiments: (a) when the binder used to form the granulate is starch it is preferred to use an amount that provides the product formulation with from about 10 wt. % to about 20 wt. % starch; (b) when the binder used to form the granulate is providone K30 it is preferred to use an amount that provides the product formulation with from about 3 wt. % to about 10 wt. % of providone K30; and (c) when the binder used to form the granulate is hypromellose 2910, 6 cps, it is preferred to use an amount that provides the product formulation with from about 3 wt. % to about 10 wt. % of hypromellose 2910, 6 cps.

In one aspect the invention provides a granulate comprising a crystalline hydrochloride salt of (5S,8S)-8-[{(1R)-1-(3,5-Bis-(trifluoromethyl)phenyl)-ethoxy}-methyl]-8-phenyl-1,7-diazaspiro[4.5]decan-2-one, intragranular microcrystalline cellulose, lactose monohydrate, intragranular croscarmellose sodium and providone K30 as a binder. In some embodiments it is preferred to use as the hydrochloride salt in the granulate the monohydrate hydrochloride salt form I of (5S,8S)-8-[{(1R)-1-(3,5-Bis-(trifluoromethyl)phenyl)-ethoxy}-methyl]-8-phenyl-1,7-diazaspiro[4.5]decan-2-one. In some embodiments it is preferred to prepare the granulate such that it has a bulk density of from about 0.54 g/ml to about 0.57 g/ml and a tapped density of from about 0.67 g/ml to about 0.7 g/ml.

In some embodiments it is preferred to use a total amount of croscarmellose sodium in the formulation of from about 2 wt. % to about 8 wt. %. In some embodiments it is preferred for the wt. ratio of intragranular to extragranular croscarmellose sodium used in the formulation to be a ratio of from about 1:1 to about 1:1.5, more preferably the wt. ratio of intragranular to extragranular croscarmellose sodium is about 1:1.5.

In some embodiments it is preferred to employ microcrystalline cellulose characterized by a mean average particle diameter of less than about 70 microns as the intragranular microcrystalline cellulose. In some embodiments it is preferred to use an amount of the intragranular microcrystalline cellulose comprising from about 2 wt. % to about 20 wt. % of the product formulation. In some embodiments it is preferred to use an amount of microcrystalline cellulose that comprises about 10 wt. % of the product formulation.

In some embodiments it is preferred to employ microcrystalline cellulose characterized by a mean average particle diameter of greater than about 70 microns as the extragranular microcrystalline cellulose. In some embodiments it is preferred to use an amount of the extragranular microcrystalline cellulose comprising up to about 40 wt. % of the product formulation, preferably from about 19 wt. % to about 40 wt. % of the product formulation, and more preferably about 19 wt. % of the product formulation.

In another aspect, the present invention provides a granulate prepared by the process comprising:
(a) dry blending:
  (i) a crystalline form 1 hydrochloride monohydrate salt of (5S,8S)-8-[{(1R)-1-(3,5-Bis-(trifluoromethyl)phenyl)-ethoxy}-methyl]-8-phenyl-1,7-diazaspiro[4.5]decan-2-one (API);
  (ii) intragranular microcrystalline cellulose having a mean particle size of less than about 70 microns;
  (iii) lactose monohydrate (impalpable grade); and
  (iv) intragranular croscarmellose sodium,
  to provide a first dry-blended powder;
(b) agglomerating the first dry-blended powder prepared in Step "a" in a high shear granulator using a granulating fluid comprising water and providone K-30;
(c) forming a granulate by wet milling the agglomerate prepared in Step "b";
(d) drying the wet milled granulate from step "c"; and
(e) dry-milling the dried granulate from Step "d" to provide a granulate having an average particle size of 250 microns.

In some embodiments it is preferred to carry out the wet milling process of Step "c" using a COMIL wet mill. In some embodiments it is preferred to wet mill granulate material in Step "c" to provide granulate having an average particle size of 2 mm. In some embodiments, in Step "d" it is preferred to dry the granulate to a moisture content of less than 3.0 wt. %. In some embodiments, in Step "d" it is preferred to dry the wet-milled granulate to a residual moisture content of less than about 5.0 wt. %. In some embodiments it is preferred to provide a dried granulate in Step "d" which has a bulk density of from about 0.50 g/ml to about 0.60 g/ml and a tapped density of from about 0.65 g/ml to about 0.72 g/ml. In some embodiments it is preferred to carry out step "d" in a fluid bed dryer.

In some embodiments, during granulate preparation it is preferred to add an amount of intragranular croscarmellose sodium that is about 5.0 wt. % of the amount of API present in the first dry-blended powder. In some embodiments, during granulate preparation it is preferred to add an amount of intragranular microcrystalline cellulose that is about 25 wt. % of the amount of API present in the first dry-blended powder. In some embodiments, during granulate preparation it is preferred to add lactose monohydrate in an amount that is from about 51 wt. % to about 52 wt. % of the amount of API present in the first dry-blended powder".

In some embodiments of the process, during granulate preparation it is preferred that the granulating fluid used in Step "b" to agglomerate the first dry-blended powder from Step "a" provides an amount of providone K30 that is about 12.5 wt. % of the amount of API present in the first dry-blended powder. In some embodiments it is preferred for the agglomeration end point in step "b" to be visual confirmation that the first dry-blended powder has been consumed in the formation of agglomerate, more preferably, the agglomeration endpoint of Step "b" is the appearance of small granules without powder loss from the granulator.

In some embodiments it is preferred to prepare the granulate using an API comprising crystalline form 1 hydrochloride monohydrate salt of (5S,8S)-8-[{(1R)-1-(3,5-Bis-(trifluoromethyl)phenyl)-ethoxy}-methyl]-8-phenyl-1,7-diazaspiro[4.5]decan-2-one, which has an X-ray Powder Diffraction Pattern containing the following characteristic peaks expressed in terms of diffraction angle (in 2θ, all values reflect an accuracy of ±0.2) lattice "d" spacing (in angstroms) and relative peak intensities ("RI"):

| Diffraction angle (2θ, ± 0.2 | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Weak | 3.78. |

Another aspect of the present invention is the provision of a tablet made by direct compression of a powder pharmaceutical formulation comprising a dry blend of:

(a) a granulate comprising crystalline hydrochloride monohydrate salt of (5S,8S)-8-[{(1R)-1-(3,5-Bis-(trifluoromethyl)phenyl)-ethoxy}-methyl]-8-phenyl-1,7-diazaspiro[4.5]decan-2-one, microcrystalline cellulose, lactose monohydrate, and a disintegrant selected from sodium starch glycolate and croscarmellose sodium, wet granulated with an aqueous binder solution; and (b) microcrystalline cellulose, a disintegrant selected from sodium starch glycolate and croscarmellose sodium, and magnesium stearate, wherein the formulation provides a pressed tablet having a hardness of at least 10 kp (kilopond).

In one aspect, the present invention provides a tablet comprising: (a) a granulate comprising: at least one crystalline salt of Formula I; intragranular is microcrystalline cellulose; lactose monohydrate; intragranular disintegrant; and a binder; and (b) extragranular microcrystalline cellulose; extragranular disintegrant; and magnesium stearate, wherein the tablet has a hardness of at least 10 kp and a friability of less than 0.8%. In some embodiments it is preferred for the crystalline salt of Formula I comprising the tablet to comprise a monohydrate hydrochloride salt. In some embodiments it is preferred for said intragranular and extragranular disintegrant to be croscarmellose sodium. In some embodiments it is preferred for the intragranular microcrystalline cellulose used to prepare the tablet to be characterized by a mean average particle diameter of less than about 70 microns. In some embodiments it is preferred for the extragranular microcrystalline cellulose used to prepare the tablet to be characterized by a mean average particle diameter of greater than about 70 microns.

In some embodiments it is preferred to press a tablet having a hardness of from about 10 kp to about 16 kp and a friability of less than 0.8%. In some embodiments it is preferred to press a shaped tablet having tabular projections, and wherein the tablet has a hardness of from about 10 kp to about 16 kp and a friability of less than 0.8%. In some embodiments it is preferred to press a tablet containing an amount of crystalline form 1 hydrochloride monohydrate salt of of (5S,8S)-8-[{(1R)-1-(3,5-Bis-(trifluoromethyl)phenyl)-ethoxy}-methyl]-8-phenyl-1,7-diazaspiro[4.5]decan-2-one providing a 100 mg dose of the hydrochloride monohydrate which provides the following dissolution profile in 900 mL of dissolution medium comprising 0.25% sodium dodecyl sulfate solution buffered with 0.05 M sodium acetate at pH 4.5, determined using a USP 2 Apparatus Paddle Stirrer, without sinkers, operated at 75 RPM:

| Time (min.) | Average (% of active initially present released) | Range of % active released over 6 samples |
|---|---|---|
| 10 | 92% | 89%-95% |
| 20 | 97% | 95%-101% |
| 30 | 97% | 96%-101% |
| 45 | 98% | 96%-102% |
| 60 | 100% | 97%-103% |

In some embodiments it is preferred to supply the tablet with a film coating, preferably a film coating comprising a hydroxypropylmethyl cellulose-based (HPMC-based) coating material, more preferably the HPMC-based coating material is selected from Opadry II White®, Opadry II Pink®, and Opadry Fx Purple®. In embodiments in which tablets are supplied with an HPMC-based coating it is preferred for coated tablets to comprise an amount of crystalline form 1 hydrochloride monohydrate salt of (5S,8S)-8-[{(1R)-1-(3,5-Bis-(trifluoromethyl)phenyl)-ethoxy}-methyl]-8-phenyl-1,7-diazaspiro[4.5]decan-2-one providing a 100 mg dose of the hydrochloride monohydrate which provides the following dissolution profile in 900 mL of dissolution medium comprising 0.25% sodium dodecyl sulfate solution buffered with 0.05 M sodium acetate at pH 4.5 determined using a USP 2 Apparatus Paddle Stirrer, without sinkers, operated at 75 RPM:

| Time (min.) | Average (% of active initially present released) | Range of % active released over 6 samples |
|---|---|---|
| 10 | 93% | 92%-94% |
| 20 | 98% | 95%-100% |
| 30 | 98% | 95%-100% |
| 45 | 99% | 96%-101% |
| 60 | 100% | 97%-102% |

Another aspect of the present invention is the provision of a method of treating and/or preventing emesis and/or nausea in a mammal comprising administering a therapeutically effective amount of any of the above-described formulations and tablets.

DETAILED DESCRIPTION OF THE INVENTION

As mentioned above, the preparation of NK-1 receptor antagonists compound of Formula I has been described in U.S. Pat. No. 7,049,320, issued May 23, 2006 (the '320 patent) and in an international application co-filed with the present application under Attorney's docket no. CD06628, each of which is incorporated herein by reference in its entirety.

Formula I

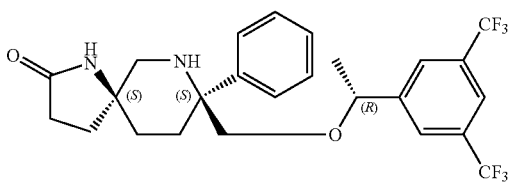

Preparation of salts of (5S,8S)-8-[{(1R)-1-(3,5-Bis-(trifluoromethyl)-phenyl)-ethoxy}-methyl]-8-phenyl-1,7-diazaspiro[4.5]decan-2-one (salts of the compound of Formula I), including the monohydrate hydrochloride salt of Formula II (shown below) and various tosylate salts, have been described in provisional application nos. 60/789,280 and 60/789,513, each of which was filed on Apr. 5, 2006, each of which is incorporated herein by reference in its entirety. While the present invention may be carried out using numerous salts of the compound of Formula I, in some embodiments it is preferred to employ the hydrochloride salt of the compound of Formula II, more preferably, a crystalline hydrochloride monohydrate salt form I of (5S,8S)-8-[{(1R)-1-(3,5-Bis-(trifluoromethyl)phenyl)-ethoxy}-methyl]-8-phenyl-1,7-diazaspiro[4.5]decan-2-one (the hydrochloride monohydrate compound of Formula II)

Formula II

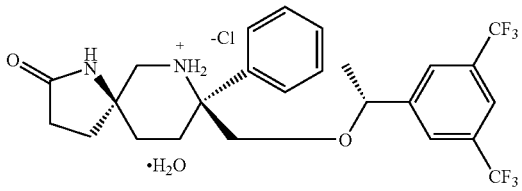

having an X-ray Powder Diffraction spectrum containing characteristic peaks present at a diffraction angle equal to those shown in Table I, expressed in terms of 2 θ (all values reflect an accuracy of ±0.2), with the associated lattice "d" spacing (in angstroms) and relative peak intensities ("RI").

TABLE I

| Diffraction angle (2θ, ± 0.2) | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Weak | 3.78. |

The provision of this hydrocholoride salt is described in detail in the above-mentioned provisional application no 60/798, 280, and in the above-mentioned international application co-filed herewith under attorney's docket no. CD06628.

The inventors have surprisingly found that a suitable tablet can be prepared which, contains, as an active pharmaceutical ingredient (API), a salt of (5S,8S)-8-[{(1R)-1-(3,5-Bis-(trifluoromethyl)phenyl)-ethoxy}-methyl]-8-phenyl-1,7-diazaspiro[4.5]decan-2-one by providing a granulate comprising the API, which granulate, when admixed with a compression aid, a disintegrant, and a lubricant, provides a compressible powder formulation suitable for providing, by direct compression, a tablet suitable for oral administration which is believed to have useful pharmacokinetic (PK) properties, and has suitable dissolution properties to prevent and/or treat nausea and/or emesis, for example, in the treatment and/or prevention of delayed phase chemically induced nausea and emesis (CINE).

A granulate containing the API, suitable for use in the compressible formulation of the present invention can be prepared using the process diagramed in Scheme I, Steps 1 to 4. The granulate is then blended with an extragranular compression aid and an extragranular disintegrant, and the blended powder thus prepared is blended with a lubricant to provide a suitable compressible formulation.

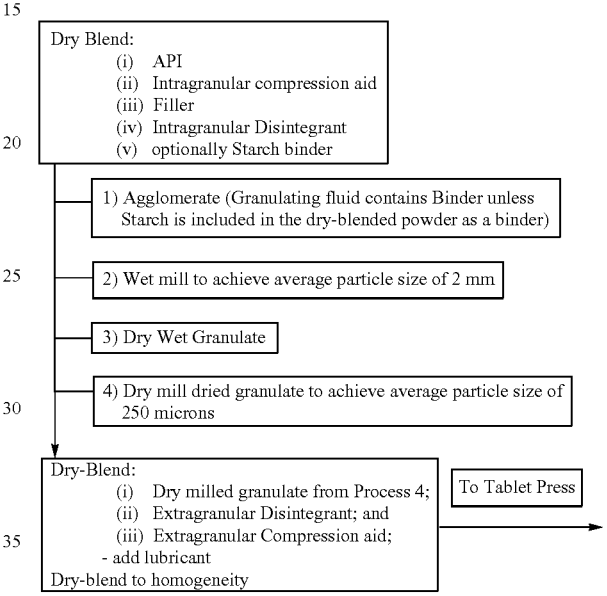

Scheme I

In accordance with steps 1 to 4 of Scheme I, preparation of the granulate is a process comprising forming a first dry-blended powder by dry blending the API, an intragranular compression aid, an intragranular disintegrant, and a filler. In some embodiments it is preferred to use an API which is in the form of a crystalline monohydrate hydrochloride salt. In some embodiment, after the constituents of the first dry-blended powder are intimately mixed, the powder is agglomerated by wet-granulating the powder in a high-shear granulator using a granulating fluid containing a binder. In some embodiments, following agglomeration, it is preferred to wet-mill the agglomerated material using a COMIL wet mill to provide a granulate product having an average particle size of 2 mm. In some embodiments, following wet-milling, it is preferred to dry the wet granulate in a fluid bed dryer. In some embodiments it is preferred to dry the wet-milled granulate to a residual moisture content of less than about 5.0 wt. %. In some embodiments it is preferred to dry the granulate to a residual moisture content of less than about 3.0 wt. %. In some embodiments, following drying, it is preferred to dry-milled the dried granulate, thereby providing an API-containing granulate having an average particle size of about 250 microns. When an API-containing granulate having an average particle size of 250 microns is provided, preferably, the API-containing granulate has a particle size distribution of from about 50 microns to about 850 microns.

Following Step (4) of Scheme I, in the second stage of preparing a compressible formulation of the invention, the dry-milled and classified granulate is dry-blended with a compression aid (extragranular compression aid) and a disintegrant (extragranular disintegrant) until a homogeneous powder is formed. Lubricant is then added to the homogeneous powder and the admixture is blended again until homogeneous, providing a powder formulation that is suitable for preparing tablets by direct compression (compressible pharmaceutical formulation).

Next, the constituents of the granulate and compressible formulation as well as details of tableting and tablets produced from the compressible formulation are discussed in greater detail.

As mentioned above, the compressible formulation includes an API-containing granulate comprising the API, an intragranular compression aid, an intragranular disintegrant, and a filler, preferably a lactose monohydrate filler. In some embodiments of the present invention it is preferred for the API to be crystalline monohydrate hydrochloride salt form I of the compound of Formula I. Crystalline monohydrate hydrochloride salt form I suitable for use in the formulations of the invention can be prepared as described in U.S. provisional Patent Application No. 60/789,280 (the '280 application), filed Apr. 5, 2006, and incorporated herein by reference in its entirety. It will be appreciated that other forms of the API can be employed in the tablets and compressible formulation of the present invention, including other salt forms, amorphous to forms, and the free base form of the API, the preparation of which is described in one or more of the abovementioned '320 patent, '280 application, and U.S. provisional application No. 60/789,513, filed Apr. 5, 2006, each of which is incorporated herewith in its entirety. In some embodiments it is preferred to provide the API in a crystal size with the desirable size range either by micronizing API having a larger average crystal size, or by precipitating the crystals in a controlled crystallization to produce crystals having the desired average crystal size and a desired particle size range. Preferably, API suitable for use in tablet formulations of the invention has an average crystal size of from about 40 microns to about 100 microns, more preferably, an average crystal size of about 80 microns.

In some embodiments using lactose monohydrate as a filler, preferably impalpable grade (typically 450 mesh) is used, and preferably it is used in an amount of up to about 20 wt. % of the formulation, although lesser amounts can be used or the filler can be eliminated. In some embodiments it is preferred to use an amount of the filler that provides about 20.5 wt. % of lactose monohydrate to the finished tablet.

In some embodiments, the intragranular compression aid added to the first dry-blended powder is preferably a microcrystalline cellulose with a small average particle size, selected to provide good binding of the API within the granulate. It will be appreciated that, upon agglomeration of the first dry-blended powder, some or all of the added intragranular compression aid will lose its characteristic particle size in the agglomeration process as it is incorporated into granules formed in the agglomeration process. In some embodiments the intragranular compression aid added to the first dry-blended powder is preferably a microcrystalline cellulose characterized by an average particle size of less than about 70 microns, more preferably an average particle size of less than about 57 microns, and further characterized by a bulk density of less than about 0.35 g/ml and a tapped density of about 0.41 g/ml. Examples of commercially available compression aids suitable for use an intragranular microcrystalline cellulose in the formulations of the present invention include, but is not limited to, Avicel PH 101 (FMC Biopolymer), which is characterized by a mean particle size of about 56.3 microns, a bulk density of about 0.34 g/ml and a tapped density of about 0.41 g/ml.

In some embodiments it is preferred to add an amount of intragranular compression aid to the granulate that provides from about 8 wt. % to about 20 wt. % of the weight of the compressible formulation produced. Preferably, the intergranulate compression aid is added in an amount that comprises from about 12.7 wt. % to about 13.2 wt. % of the granulate into which it is incorporated, more preferably about 12.9 wt. % of the granulate into which it is incorporated.

In some embodiments it is preferred for the intragranular disintegrant to be selected from sodium starch glycolate and croscarmellose sodium, more preferably it is croscarmellose sodium. The intragranular disintegrant and the extragranular disintegrant (discussed in detail below) are preferably selected to be the same constituent material, albeit having a different physical specification, for example, different average particle size and density. In some embodiments of the compressible formulation, the total amount of disintegrant employed (sum of the amounts of extragranular and intragranular disintegrant used) is from about 2 wt. % of the compressible formulation to about 8 wt. % of the compressible formulation.

In embodiments using croscarmellose sodium as the intragranular disintegrant, it is preferably used in an amount of from about 1.3 wt. % of the granulate to about 5.2 wt. % of the finished granulate, more preferably it is used in an amount that is from about 2.4 wt. % to about 2.8 wt. % of the finished granulate and more preferably it is used in an amount that is about 2.58 wt. % of the finished granulate. Relative to the compressible formulation, preferably the intragranular disintegrant is used in an amount that provides about 2 wt. % of the compressible formulation.

In some embodiments the binder is preferably selected from pregelatinized starch, providone K30, and a hydroxypropylmethyl cellulose (hypromellose), more preferably the binder is providone K30. With reference to Scheme I, when starch is selected as the binder, it is preferably added as a powdered constituent and homogeneously blended into the first dry-blended powder. When either providone or hypromellose is selected as a binder, it is preferably added to the granulate by dissolving it in the granulating fluid used to agglomerate the first dry-blended powder.

In some embodiments, when pregelatinized starch is employed as a binder, preferably it is dry-blended into the first dry-blended powder in an amount that provides from about 10 wt. % to about 20 wt. % of the finished granulate. When the first dry-blended powder contains starch, agglomeration is carried out by using purified water as the granulating fluid, which solubilizes the binder contained in the first dry-blended powder, agglomerating the first dry-blended powder.

In some embodiments using hydroxypropylmethyl cellulose as a binder, preferably hypromellose 2910, 6 cps is selected, although other grades may alternatively be employed. When hypromellose 2910, 6 cps is used, preferably it is used in an amount that provides from about 3 wt. % to about 6 wt. % of the granulate. In general, when hypromellose is used as a binder it is used to agglomerate the homogenous blend of granulate constituents as a water solution containing from about 12 wt % to about 13 wt. % of hypromellose 2910, 6 cps.

In some embodiments using providone as a binder, preferably providone K30 is used, preferably in an amount that provides from about 3 wt. % to about 10 wt. % of the granulate, more preferably from about 6 wt. % to about 7 wt. % of the granulate, more preferably about 6.6 wt. % of the granulate. In general, when providone K30 is used as a binder it is used to agglomerate the homogenous blend of granulate constituents as a water solution containing about 16.7 wt. % of providone K30.

The constituents, relative amounts of constituents used in the granulate composition, and the conditions used to agglomerate and prepare the granulate are selected, guided by the foregoing description of relative constituent amounts, types of constituents, and methods of agglomerating, milling, and classifying the resulting granulate composition, to provide a dried granulate which has a bulk density of from about 0.5 g/ml to about 0.6 g/ml, preferably from about 0.54 g/ml to about 0.57 g/ml, and a tapped density of from about 0.65 g/ml to about 0.72 g/ml, preferably from about 0.67 g/ml to about 0.70 g/ml when measured using standard techniques for measuring the bulk and tapped density of granular solids. Without wanting to be bound by theory, it is believed that granulate when prepared in accordance with the present process, granulate having bulk and tapped density within these ranges provides a compressible formulation yielding tablets of the invention having low friability and suitable hardness while maintaining acceptable dissolution properties.

In some embodiments of the present process, following the provision of an API-containing granulate, the granulate is dry-mixed with extragranular compression aid and extragranular disintegrant to form a homogeneous powder which is then dry-blended with an aliquot of a lubricant, preferably magnesium stearate, to again form a homogeneous powder. When magnesium stearate is employed as the lubricant it is preferably classified using a 20 mesh sieve before it is blended into the formulation. In some embodiments it is preferred to employ an amount of magnesium stearate that provides less than about 1.0 wt. % of the compressible formulation, more preferably about 0.5 wt. % of the final formulation.

In some embodiments, mentioned above, preferably the extragranular disintegrant is selected from sodium starch glycolate and croscarmellose sodium, more preferably, the extragranular disintegrant is crocarmellose sodium. Preferably the extragranular disintegrant is selected to be the same material as the intragranular disintegrant used to prepare the API-containing granulate (granulate). In some embodiments it is preferred to use an amount of extragranular disintegrant that, taken together with the amount of intragranular disintegrant employed to make the granulate, provides from about 2 wt. % of the compressible formulation to about 8 wt. % of the compressible formulation. In some embodiments using croscarmellose sodium, it is preferred to use an amount of croscarmellose sodium that provides about 3 wt. % of the compressible formulation.

In some embodiments it is preferred for the extragranular compression aid (microcrystalline cellulose) to be characterized by an average particle size of greater than about 70 microns, preferably greater than about 100 microns, and more preferably having an average particle size greater than about 113 microns, and further characterized by a bulk density of about 0.36 g/ml, and a tapped density of about 0.42 g/ml. Examples of commercially available microcrystalline cellulose materials which are suitable include Avicel PI-1102, which has an average particle size of about 113.8 microns, a bulk density of about 0.36 g/ml, and a tapped density of about 0.42 g/ml. In some embodiments it is preferred to use an amount of the extragranular compression aid that provides a suitable tablet hardness and friability in a tablet made from the compressible formulation, preferably a tablet having a hardness of from about 10 kp (kiloponds) to about 16 kp and a friability of less than about 0.8%. In some embodiments it is preferred to use an amount of extragranular compression aid that provides up to about 40 wt. % of the compressible formulation, more preferably from about 19 wt. % to about 40 wt. % of the compressible formulation, more preferably, an amount that provides about 19 wt. % of the compressible formulation.

In some embodiments it is preferred to use the tablet formulation shown below in Table II, which lists first the amounts of the constituents of the granulate followed by the amounts of the extragranular constituents of the compressible formulation from which tablets of the invention can be made via direct compression process. The entries of constituent weights in Table II reflect grams of constituent present in an amount of the compressible formulation included in a single tablet. The weights are scaled up geometrically for preparing the compressible formulation in bulk, and in general it is preferred to formulate up to 50 kg of the compressible formulation in a manufacturing run.

TABLE II

| No. | Ingredients | Grams |
|---|---|---|
| 1. | API | 100.00 |
| 2. | Microcrystalline Cellulose (e.g. Avicel PH 101) (Intragranular) | 25.00 |
| 3. | Croscarmellose Sodium (Intragranular) | 5.00 |
| 4. | Lactose Monohydrate (Impalpable) | 51.25 |
| 5 | Povidone (K-30) (--- wt. % in purified water - evaporated) Process - agglomerate and mill | 12.50 |
|  | Granulate | 193.75 g |
| 6. | Croscarmellose Sodium (Extragranular) | 7.5 g |
| 7. | Magnesium Stearate | 1.25 g |
| 8. | Microcrystalline Cellulose (e.g. Avicel PH 102) (Extragranular) | 47.5 g |
| 9. | Purified water (Evaporated) | — |
|  | Compressible Formulation | 250 g |
|  | Direct Compression Core Tablets- compressible powder aliquot | 250.0 mg |
| 10. | Opadry II White ® Y-30-18037 | 7.5 |
| 11. | Purified water (Evaporated) | — |
|  | Coated tablets | 257.5 mg* |

*Note: coating shown is for oval tablets, when leaf-shaped tablets are pressed they are coated with a combination of 7.5 mg Opadry II Pink ® and 7.5 mg Opadry fx Purple ® on a 250 mg core, yielding a 265 mg coated tablet.

In some embodiments it is preferred to use the tablet formulation shown below in Table III, which lists first the amounts of the constituents of the granulate, followed by the amounts of the extragranular constituents of the compressible formulation from which tablets of the invention can be made via direct compression process. The entries of constituent weights in Table III reflect grams of constituent present in an amount of the compressible formulation included in a single tablet. Although the formulation can be employed to form tablets containing other amounts of API, the formulation shown in Table III will be best utilized when employed to form tablets containing at least about 200 mg of the API. The weights of the excipients shown in Table III can be scaled up geometrically for preparing the compressible formulation in bulk, and in general it is preferred to formulate up to 50 kg of the compressible formulation in a manufacturing run.

TABLE III

| No. | Ingredients | Grams |
|---|---|---|
| 1. | API | 200.00 |
| 2. | Microcrystalline Cellulose (e.g. Avicel PH 101) (Intragranular) | 50.00 |

TABLE III-continued

| No. | Ingredients | Grams |
|---|---|---|
| 3. | Croscarmellose Sodium (Intragranular) | 10.00 |
| 4. | Lactose Monohydrate (Impalpable) | 102.50 |
| 5 | Povidone (K-30) (--- wt. % in purified water - evaporated) | 25.00 |
|   | Process - agglomerate and mill | |
|   | Granulate | 387.50 g |
| 6. | Croscarmellose Sodium (Extragranular) | 10.50 g |
| 7. | Magnesium Stearate | 2.00 g |
| 8. | Purified water (Evaporated) | — |
|   | Compressible Formulation | 400 g |
|   | Direct Compression Core Tablets- compressible powder aliquot | 400.0 mg |
| 9. | Opadry II White ® Y-30-18037 | 7.5 |
| 10. | Purified water (Evaporated) | — |
|   | Coated tablets | 407.5 mg* |

*Note: coating shown is for oval tablets, when leaf-shaped tablets are pressed they are coated with a combination of 7.5 mg Opadry II Pink ® and 7.5 mg Opadry fx Purple ® on a 400 mg core, yielding a 415 mg coated tablet.

The inventors have surprisingly found that when povidone K30 is selected as the binder, and magnesium stearate is used as a lubricant at 0.5 wt. % or less in the final formulation, the above-described compressible formulations are suitable for preparation of tablets by a direct compression process, which tablets are robust, having acceptable hardness and low friability. The formulation of the invention can provide direct compression tablets having a hardness of from about 10 kp (kilopond) to about 16 kp and friability of less than about 0.8% using conventional round dies as well as using dies imparting an elliptical shape to the tablet. Examples of tablets having an elliptical shape include, but are not limited to, tablets having an ovular shape and tablets having a "leaf-shape". Leaf-shaped tablets comprise a circular or ovular central portion from which are, for example, "horn-shaped", or can be described as "tabular" projection extending from the central portion of the tablets. Although such distinctive shapes are valuable for providing quick visual identification of the medicament, and may make it easier for those with digital impairment, for example, poor fine motor skills or gloved hands, to grasp and manipulate the dosage form, the projecting portions of such tablets concentrate mechanical forces in the projecting portion of the tablet. Accordingly, such tablets have a tendency to "chip" in the extremes of the projecting portion or have material crack away from the central portion of the tablet during handling and storage, thus present a problem due to high friability and/or unacceptable cosmetic and aesthetic presentation to the end user. The formulation of the present invention described above surprisingly provides elliptical-shaped tablets having friability of less than about 0.8% under testing conditions performed in accordance with the standards of the pharmaceutical industry (see USP chapter 1216), and a hardness of from about 10 kp to about 16 kp. Surprisingly, tablets of this configuration having low friability and hardness within this range are available using compression pressures in the range of from about 9 kN to about 18 kN with the compressible formulation of the invention. Moreover, tablets having these mechanical properties have acceptable dissolution properties also.

EXAMPLES

Standard pharmaceutical manufacturing processes were utilized in the preparation of formulations of the present invention. Dry blending and agglomeration was carried out in a high shear granulator manufactured by Fielder. Wet milling was carried out in a wet mill manufactured by COMIL. Fluid bed drying was carried out in a laboratory scale fluid bed dryer manufactured by Glatt Air Technology. Classifying and sieving operations were carried out in manually operated sieve equipment having functionality according with standard practice in the pharmaceutical industry. Dry milling operations were carried out in a laboratory scale mill manufactured by COMIL and equipped with a 14 mesh screen.

Unless noted to the contrary, all materials utilized in the formulations were articles of commerce meeting the current requirements of the United States Pharmacopeia/National Formulary (USP/NF).

The active pharmaceutical ingredient (API) used in preparing the example formulations was prepared in accordance with the processes described in each of U.S. provisional patent application No. 60/789,280 and U.S. provisional application No. 60/919,666, filed Mar. 22, 2007.

The API used in the examples is the Form I monohydrate hydrochloride salt form of (5S,8S)-8-[{(1R)-1-(3,5-Bis-(trifluoromethyl)phenyl)-ethoxy}-methyl]-8-phenyl-1,7-diaza-spiro[4.5]decan-2-one having characteristic X-ray Powder Diffraction peaks present at a diffraction angle equal to those shown in Table IV, expressed in terms of 2θ all values reflect an accuracy of ±0.2), with the associated lattice "d" spacing (in angstroms) and relative peak intensities ("RI"):

TABLE IV

| Diffraction angle (2θ, ±0.2) | RI | Lattice Spacing (Å ± 0.04) |
|---|---|---|
| 16.1 | Medium | 5.49 |
| 18.4 | Medium | 4.83 |
| 21.6 | Strong | 4.11 |
| 23.5 | Weak | 3.78. |

Example 1

Powder Formulation Suitable for Tableting

A powder formulation suitable for providing tablets by direct compression was prepared by placing into a Fielder granulator 100 mg of the above-described API which had been classified through a 20 mesh sieve. Added to the API was 25 mg of Avicel PH101 microcrystalline cellulose, 51.25 mg of lactose monohydrate (impalpable grade, NF—Formost Farms, used as received), and 5 mg of croscarmellose sodium (FMC, NF/Ph. Eur. grade, grade). The granulator was operated to dry-blend the constituents and provide a homogeneous blend. After obtaining a homogeneous blend the dry-blended powder was agglomerated by operating the granulator using a granulating fluid consisting of 12.5 mg of providone K30 dissolved in 62.5 ml of distilled water. The granulator was operated to agglomerate the powder until small granules were observed with no loss of powder.

The wet agglomerated powder was discharged into a COMIL wet mill and wet milled to provide a granulate having an average particle size of 2 mm. The wet milled granulate was transferred into a Glatt Air Technologies fluid bed dryer and dried until the granulate had a residual moisture content of less than 5.0 wt. % loss on drying, then dry-milled in the COMIL laboratory mill to provide a granulate with an average particle size of 250 microns and a particle size distribution of 50 microns to 850 microns. The granulate thus obtained was found to have a bulk density of 0.55 g/ml and a tapped density of 0.70 g/ml.

The milled granulate prepared above (192 mg) was charged into a Fielder granulator along with 47.5 mg of Avicel PH102 microcrystalline cellulose and 7.5 mg of croscarmellose sodium (both from FMC, NF/Ph. Eur grade, used as received), and the granulator operated to provide a homogeneous blend of the dry constituents. When a homogeneous powder had been obtained, 1.25 mg of magnesium stearate (Mallinckrodt, NF, non-bovine, classified through a 20 mesh sieve prior to use) was added to the granulator and blended until a homogeneous powder was obtained.

Example 2a

Tablet Preparation

Tablet cores containing 100 mg of API each were prepared by placing a 250 mg aliquot of the powder prepared in Example 1 above into a tablet press (Key Press) equipped with an oval-shaped die (Elizabeth Carbide) and compressing the powder into a tablet. These tablets were tested for hardness (breaking force) under testing conditions performed in accordance with the standards of the pharmaceutical industry (see USP chapter 1217) and found to have a hardness of between 10 kp and 16 kp and were tested for friability under testing conditions performed in accordance with the standards of the pharmaceutical industry (see USP chapter 1216) and found to have a Friability of less than 0.8%.

In the same manner, tablet cores containing 100 mg of API each were prepared by placing a 250 mg aliquot of the powder prepared in Example 1 above into the tablet press equipped with a leaf-shaped die (Elizabeth Carbide), and pressing the powder into a tablet having a hardness of 10 kp to 16 kp. These leaf-shaped tablets were tested for hardness (breaking force) under testing conditions performed in accordance with the standards of the pharmaceutical industry (see USP chapter 1217) and found to have a hardness of between 10 kp and 16 kp. These tablets were tested for friability under testing conditions performed in accordance with the standards of the pharmaceutical industry (see USP chapter 1216) and found to have a Friability of less than 0.8%.

A number of the oval-shaped tablets prepared above were selected for dissolution testing. A USP 2 Apparatus Paddle Stirrer was used for dissolution testing. A 6 sample average dissolution profile in 900 mL of dissolution medium comprising 0.25% sodium dodecyl sulfate solution buffered with 0.05 M sodium acetate at pH 4.5 determined using a the USP 2 Apparatus Paddle Stirrer, without sinkers, operated at 75 RPM. The results of these dissolution tests are presented in Table V.

TABLE V

| Time (min.) | Average (% of active initially present released) | Range of % active released over 6 samples |
| --- | --- | --- |
| 10 | 92% | 89%-95% |
| 20 | 97% | 95%-101% |
| 30 | 97% | 96%-101% |
| 45 | 98% | 96%-102% |
| 60 | 100% | 97%-103% |

These data show that the compressed tablets having acceptable hardness, and friability also have acceptable dissolution properties.

Example 2b

Tablet Coating

A water dispersion was prepared comprising 20% w/w of Opadry II white (Colorcon, used as received) in purified water. Oval 250 mg tablet cores prepared in Example 1 were coated in a fully perforated coating pan adjusting the inlet air temperature and flow and the outlet air flow to maintain the product bed temperature at a temperature between 45° C. and 50° C. Spraying was continued until a calculated coating weight of 3.0% was applied to the tablet cores.

A number of the coated tablets thus prepared were selected for dissolution testing. A USP 2 Apparatus Paddle Stirrer was used for dissolution testing. A 6 sample average dissolution profile was obtained in 900 mL of dissolution medium comprising 0.25% sodium dodecyl sulfate solution buffered with 0.05 M sodium acetate at pH 4.5 using the USP 2 Apparatus Paddle Stirrer, without sinkers, operated at 75 RPM. The results of these dissolution tests are presented in Table VI.

TABLE VI

| Time (min.) | Average (% of active initially present released) | Range of % active released over 6 samples |
| --- | --- | --- |
| 10 | 93% | 94%-92% |
| 20 | 98% | 95%-100% |
| 30 | 98% | 95%-100% |
| 45 | 99% | 96%-101% |
| 60 | 100% | 97%-102% |

These data show that the coated tablets had the same acceptable dissolution properties as the uncoated cores.

It will be found that administration of a sufficient number of the tablets prepared above to provides a therapeutically effective serum level of the API will be effective in treating and/or preventing nausea and/or emesis in a patient in need of such treatment and/or prevention.

The above description of the invention is intended to be illustrative and not limiting. Various changes or modifications in the embodiments described herein may occur to those skilled in the art. These changes can be made without departing from the scope or spirit of the invention.

What is claimed is:

1. A powdered pharmaceutical formulation comprising: (a) a granulate comprising: at least one crystalline salt of (5S, 8S)-8-[{(1R)-1-(3,5-bis-(trifluoromethyl)phenyl)-ethoxy}-methyl]-8-phenyl-1,7-diazaspiro[4.5]decan-2-one; intragranular microcrystalline cellulose, optionally wherein the microcrystalline cellulose has a mean average particle diameter of less than about 70 microns; lactose monohydrate; a first disintegrant; and a binder; and dry-blended therewith (b) extragranular microcrystalline cellulose, optionally wherein the microcrystalline cellulose has a mean average particle diameter of greater than about 70 microns; a second disintegrant; and magnesium stearate, wherein optionally the wt. ratio of first disintegrant to second disintegrant is about 1:1.5 and wherein the formulation provides, upon compression in a tablet press, a pressed tablet having a hardness of at least 10 kp.

2. The formulation of claim 1 wherein said first and said second disintegrant are croscarmellose sodium and said binder is selected from povidone K30, pregelatinized starch and hypromellose 2910, 6 cps, wherein: (a) when the binder used to form the granulate is starch it is used in an amount the that provides the formulation with from about 10 wt. % to about 20 wt. % starch; (b) when the binder used to form the granulate is povidone K30 it is used in an amount that provides the formulation with from about 3 wt. % to about 10 wt. % of povidone K30; and (c) when the binder used to form the granulate is hypromellose 2910, 6 cps, it is used in an amount that provides the formulation with from about 3 wt. % to about 6 wt. % of hypromellose 2910, 6 cps.

3. The formulation of claim 1, wherein the intragranular microcrystalline cellulose is used in an amount comprising from about 8 wt. % to about 20 wt. % of the formulation and wherein optionally the extragranular microcrystalline cellulose is used in an amount comprising from about 19 wt. % to about 40 wt. % of the formulation.

4. The formulation of claim 1, wherein said granulate is prepared by a process comprising:
(a) dry blending:
   (i) a crystalline form 1 hydrochloride monohydrate salt of (5S,8S)-8-[{(1R)-1-(3,5-bis-(trifluoromethyl)phenyl)-ethoxy}-methyl]-8-phenyl-1,7-diazaspiro[4.5]decan-2-one (API);
   (ii) intragranular microcrystalline cellulose having a mean particle size of less than about 70 microns;
   (iii) lactose monohydrate; and
   (iv) intragranular croscarmellose sodium
to provide a first dry-blended powder;
(b) agglomerating the first dry-blended powder prepared in Step "a" in a high shear granulator using a granulating fluid comprising water and povidone K-30, optionally wherein the amount of povidone K-30 employed is about 12.5 wt. % of the amount of API employed;
(c) forming a granulate by wet milling the agglomerate prepared in Step "b" optionally carrying out the wet-milling process until a granulate having an average particle size of 2 mm is produced;
(d) drying the wet milled granulate from step "c", and optionally carrying out the drying process until the dried granulate has a moisture content of less than about 3.0 wt. %; and
(e) dry-milling the dried granulate from Step "d" to provide a granulate having an average particle size of 250 microns;
wherein the first dry-blended powder contains intragranular croscarmellose sodium in an amount that is about 5.0 wt % of the amount of API contained in the first dry-blended powder and optionally wherein the intragranular microcrystalline cellulose present in said first dry-blended powder in an amount that is about 25 wt % of the amount of API present in the first dry-blended and optionally wherein the amount of lactose monohydrate present in said first dry-blended powder is from about 51 wt. % to about 52 wt. % of the amount of API present in said first dry-blended powder.

5. The formulation of claim 4 wherein the dried granulate in Step "d" has a bulk density of from about 0.54 g/ml to about 0.57 g/ml and a tapped density of from about 0.67 g/ml to about 0.7 g/ml.

6. The formulation of claim 1 wherein the first disintegrant and the second disintegrant comprise croscarmellose sodium and the total amount of croscarmellose sodium used in the formulation is from about 2 wt. % to about 8 wt. %, and the wt, ratio of the amount of first disintegrant to second disintegrant used is from about 1:1 to about 1:1.5.

7. The formulation of claim 1, wherein the intragranular microcrystalline cellulose is used in an amount comprising from about 8 wt. % to about 20 wt. % of the product formulation.

8. The formulation of claim 1 wherein the intragranular microcrystalline cellulose is present in said first dry-blended powder in an amount that is about 25 wt. % of the amount of API present in the first dry-blended powder.

9. A powdered pharmaceutical formulation comprising: (a) a granulate comprising: at least one crystalline salt of (5S, 8S)-8-[{(1R)-1-(3,5-bis-(trifluoromethyl)phenyl)-ethoxy}-methyl]-8-phenyl-1,7-diazaspiro[4.5]decan-2-one; intragranular microcrystalline cellulose, optionally wherein the microcrystalline cellulose has a mean average particle diameter of less than about 70 microns; lactose monohydrate; a first disintegrant; and a binder; and dry-blended therewith (b) extragranular microcrystalline cellulose, optionally wherein the microcrystalline cellulose has a mean average particle diameter of greater than about 70 microns; a second disintegrant; and magnesium stearate, wherein optionally the wt. ratio of first disintegrant to second disintegrant is about 1:1.5 and wherein the formulation provides, upon compression in a tablet press, can provide tablets with a hardness of about 10 kp.

* * * * *

UNITED STATES PATENT AND TRADEMARK OFFICE
CERTIFICATE OF CORRECTION

PATENT NO. : 8,361,500 B2  Page 1 of 1
APPLICATION NO. : 12/531966
DATED : January 29, 2013
INVENTOR(S) : Qiu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 568 days.

Signed and Sealed this
First Day of September, 2015

Michelle K. Lee
*Director of the United States Patent and Trademark Office*